US00PP15374P3

(12) United States Plant Patent
Carruth

(10) Patent No.: US PP15,374 P3
(45) Date of Patent: Nov. 30, 2004

(54) SHRUB ROSE PLANT NAMED 'WEKMORFIS'

(50) Latin Name: *Rosa hybrida*
Varietal Denomination: WEKmorfis

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/243,204

(22) Filed: Sep. 13, 2002

(65) Prior Publication Data

US 2004/0055062 P1 Mar. 18, 2004

(51) Int. Cl.[7] ..... A01H 5/00
(52) U.S. Cl. ..... Plt./102
(58) Field of Search ..... Plt./102, 141

*Primary Examiner*—Howard J. Locker
(74) *Attorney, Agent, or Firm*—Christie, Parker & Hale, LLP

(57) ABSTRACT

A new variety of Shrub rose suitable for garden decoration, having flowers of velvet dark purple coloration with a white 'eyezone'.

1 Drawing Sheet

Classification: The present invention relates to a new *Rosa hybrida* plant.

Variety denomination: The new plant has the varietal denomination 'WEKmorfis'.

BACKGROUND OF THE INVENTION

This invention relates to a new and distinct variety of Shrub Rose. The varietal denomination of the new variety is 'WEKmorfis'. It has undisseminated seedlings of my creation as its seed and pollen parents.

SUMMARY OF THE INVENTION

Among the features which distinguish the new variety from other presently available and commercial rose cultivars known to the inventor are the following combination of characteristics: its unusual velvet dark purple flower coloration, its nearly horizontal zone of lighter coloration forming a broad 'V' shaped at the petal base, its petals that recurve inward at the half open stage, its red-purple filaments and styles and its red suffusion on the rachis and the stipule. The plant has a bushy to somewhat spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKmorfis' may be asexually propagated by cuttings, budding and grafting.

COMPARISON WITH PARENTS

The new rose may be distinguished from its seed parent, an undisseminated seedling of my creation by the following combination of characteristics: whereas the undisseminated seedling bears moderately small flowers (about 3.8 to 4.9 cm. in diameter) and foliage, 'WEKmorfis' bears significantly larger flowers (about 5.7 to about 7.8 cm. in diameter) and foliage. The seed parent is a floribunda rose with a medium compact mature habit, whereas 'WEKmorfis' is classified as a shrub rose with a significantly larger and more spreading mature growing habit.

The new variety may be distinguished from its pollen parent, an undisseminated seedling of my creation by the following combination of characteristics: whereas 'WEKmorfis' bears medium sized flowers of velvet dark purple coloration with a white eye and with semidouble petalage (about 7 to 9 petals), the undisseminated seedling bears significantly larger flowers of purple-pink coloration with more double petalage (about 15 to 20 petals). The pollen parent bears foliage with a very glossy finish, whereas 'WEKmorfis' bears foliage with a semiglossy finish.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of August budded and grafted on *Rosa hybrida* var. 'Dr. Huey'. Phenotypic expression may vary with environmental, cultural and climatic conditions, as well as differences in conditions of light and soil.

FLOWER

The new variety usually bears its flowers in clusters of three to five or more per stem. Flowers are borne in regular rounded to somewhat pyramidal clusters on strong medium to moderately long stems (about 48 to about 105 cm.). Outdoors, the plant blooms abundantly and nearly continuously during the growing season. The flowers have a strong clove to spicy fragrance.

BUD

The peduncle is about 2.3 to about 4.4 cm. in length, of somewhat slender to average caliper (about 0.2 to about 0.3 cm. in diameter), and usually erect. It is moderately smooth, with many stipitate glands. Peduncle color is between 144B and 139B sometimes very lightly suffused, especially on the side exposed to the sun, with between 183C and 187C.

Before the calyx breaks, the bud is about 0.9 to about 1.3 cm. in diameter at the widest point, about 1.4 to about 1.7 cm. in length, and very pointed in shape. The surface of the bud bears some foliaceous appendages, usually with slender entire to slightly cut foliaceous parts extending beyond the tip of the bud about ¼ or more of its length. Bud color is between 144A and 139B.

The sepals are about 1.9 to about 2.7 cm. in length and about 0.5 to about 0.9 cm. in width at the widest point. The outer surface of the sepal is between 144A and 139B. The inner surface of the sepal is between 138B and 139C and covered with fine wooly tomentum; sepal margins are lined with numerous stipitate glands and hairs.

As the petals open (after the calyx breaks), the bud is about 1.7 to about 2.1 cm. in diameter at the widest point, about 2.3 to about 2.9 cm. in length, and pointed to somewhat ovoid in form. The color of the under and upper surfaces of the newly opened petals is near 60A at the center of the petal suffusing to as dark as near 59A toward the edge of the petal. At the point where the petal attaches on the under surface, there is a small zone of between 5C and 4D. At the point where the petal attaches on the upper surface, there is a slightly larger zone of near 6C. On either side of this attachment point, extending to the edge of the petal, there is a moderately wide, nearly horizontal zone of lighter coloration forming a broad 'V'. The coloration of this chevron is between 37C and 39C.

BLOOM

When fully open, the bloom ranges from about 5.7 to about 7.8 cm. in diameter. Petalage is semi-double with about 7 to 9 petals and about 1 to 2 petaloids irregularly arranged. When partially open, the bloom form is very cupped to somewhat globular, and the petals are loosely cupped with petal edges moderately reflexed inward to somewhat undulated. When fully open, the bloom form is more loosely cupped, and the petals are less cupped with petal edges slightly reflexed outward to slightly undulated.

PETALS

The substance of the petals is moderately heavy and of somewhat thick thickness, with upper surfaces moderately velvety to somewhat satiny and under surfaces usually matte to slightly shiny. The outer and inner petals are broadly obovate to somewhat oval in shape with rounded apices. The petals are about 2.8 to about 3.4 cm. in length and about 1.9 to about 2.9 cm. in width at the widest point. Petal margins are entire.

NEWLY OPENED FLOWER

The under surface of the outer, intermediate and inner petals is between 71A and 70A. At the point where the petal attaches, there is a moderately small zone of between 4C and 6D.

The upper surface of the outer, intermediate and inner petals is between 71B and 64A near the center of the petal that gradually suffuses to darker than between 71A and 187A toward the edge of the petal. At the point where the petal attaches, there is a large zone of between 12D and 155D. On either side of this attachment point, extending to the edge of the petal, there is a moderately wide, nearly horizontal zone of lighter coloration forming a broad 'V'. The coloration of this chevron is between 69D and 76D.

The general tonality of the newly opened flower is between 71B and 64A near the center of the petal that gradually suffuses to darker than between 71A and 187A toward the edge of the petal. At the very center of the flower, there is a 'eyezone' pattern consisting of the basal attachment zone of between 12D and 155D and the chevron marking of between 69D and 76D in coloration.

THREE-DAY-OLD FLOWER

The under surface of the outer and inner petals is between 77A and 70A. At the point where the petal attaches, there is a moderately small zone of between 155B and 155D.

The upper surface of the outer and inner petals is between 78B and 64A near the center of the petal that gradually suffuses to darker than between 79A and 70A toward the edge of the petal. At the point where the petal attaches, there is a large zone of between 155C and 155D. On either side of this attachment point, extending to the edge of the petal, there is a moderately wide, nearly horizontal zone of lighter coloration forming a broad 'V'. The coloration of this chevron is between 69D and 155D.

The general tonality of the three-day-old flower is between 78B and 64A near the center of the petal that gradually suffuses to darker than between 79A and 70A toward the edge of the petal. At the very center of the flower, there is a 'eyezone' pattern consisting of the basal attachment zone of between 155C and 155D and the chevron marking of between 69D and 155D in coloration.

On the spent bloom, the petals usually drop off cleanly.

In August in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 91) and are arranged regularly about the pistils; a few are mixed with petaloids. The filaments are of medium to somewhat long length (about 0.5 to about 1.0 cm.), most with anthers. Filaments are near 59B in color. The anthers are of medium size for the class and all open approximately at the same time. Anther color is near 20A when immature and between 163C and 165A at maturity. Pollen is abundant.

FEMALE REPRODUCTIVE ORGANS

Pistils vary in number (average about 30). The styles are moderately even, average in length (about 0.4 to about 0.6 cm.), average in caliper, and somewhat loosely bunched to columnar. Stigma color is between 1C and 2C. Style color is near 59A. Ovaries are usually all enclosed in the calyx.

Hips are of average length (about 1.8 to about 2.3 cm.), moderately globular in form, and between 25A and 28B in color when ripe. The hip surface is very smooth with thick fleshy walls. The sepals are moderately permanent. The seeds are irregularly rounded, smooth in texture, approximately 7 to about 10 per hip, about 0.3 to about 0.5 cm. in diameter at the widest point and between 160C and 162C in color.

FOLIAGE

The compound leaves are usually comprised of three to five or more leaflets and are borne abundantly. The five-leaflet leaves are about 10.2 to about 13.3 cm. in length and about 6.8 to about 8.9 cm. in width at the widest point, somewhat heavy and leathery in texture, and semi-glossy in finish. The terminal leaflets are about 3.6 to about 5.7 cm. in length and about 2.8 to about 4.2 cm. in width at the widest point, shaped broadly ovate to somewhat oval with moderately acute to slightly acuminate apices and moderately round to somewhat acute bases. Their margins are usually simply serrate.

The upper surface of the mature leaf is between 147A and 133A. The under surface of the mature leaf is between 146B and 136C. The upper surface of the young leaf is between 137B and 136B. The under surface of the young leaf is between 146B and 133C.

The rachis is moderately light in caliper and very smooth. The upper side is shallowly grooved with many hairs and some stipitate glands on the edges of the grooves. The under side of the rachis is very smooth with many hairs and very few stipitate glands. The rachis color is between 146B and 136C. The rachis on the young leaves is sometimes very lightly suffused, especially on the side exposed to the sun, with between 183C and 187C.

The stipules are about 1.1 to about 1.7 cm. in length and moderately wide (about 0.5 to about 1.0 cm.) with moderately long straight points that usually turn out at an angle of more than 45 degrees and often recurve toward the stem. The stipules color is between 146B and 136C. The stipules on the young leaves is sometimes very lightly suffused, especially on the side exposed to the sun, with between 183C and 187C.

The petiole is about 0.9 to about 1.2 cm. in length and about 0.1 to about 0.2 cm in diameter at the widest point. The petiole color is between 146B and 136C.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy to somewhat spreading medium height growing habit (about 125 to about 140 cm. in height and about 108 to about 125 cm. spread at the widest point), with moderately full branching. It displays vigorous growth and the canes are of medium caliper for the class.

The color of the major stems is between 146B and 146D. They bear many medium size prickles that are about 0.3 to about 0.5 cm. in length. The prickles are almost straight and angled moderately downward with a somewhat short broad rounded to oval base; prickle color is between 165B and 166C. The major stem bears some small prickles of similar shape and coloration.

The color of the branches is between 144A and 137B. They bear some large prickles that are about 0.6 to about 0.8 cm. in length and of similar shape to the prickles on the major stem. The prickle color is 162C and 160B. The branches bear very few small prickles of similar shape and coloration.

The color of the new shoots is between 144B and 137B sometimes very lightly suffused with between 183C and 187C. They bear no large prickles and very few small prickles that are about 0.2 to about 0.4 cm. in length and of similar shape to the prickles on the major stems; prickle color is between 182B and 182C.

I claim:

1. A new and distinct Shrub rose plant of the variety substantially as described and illustrated herein.

* * * * *

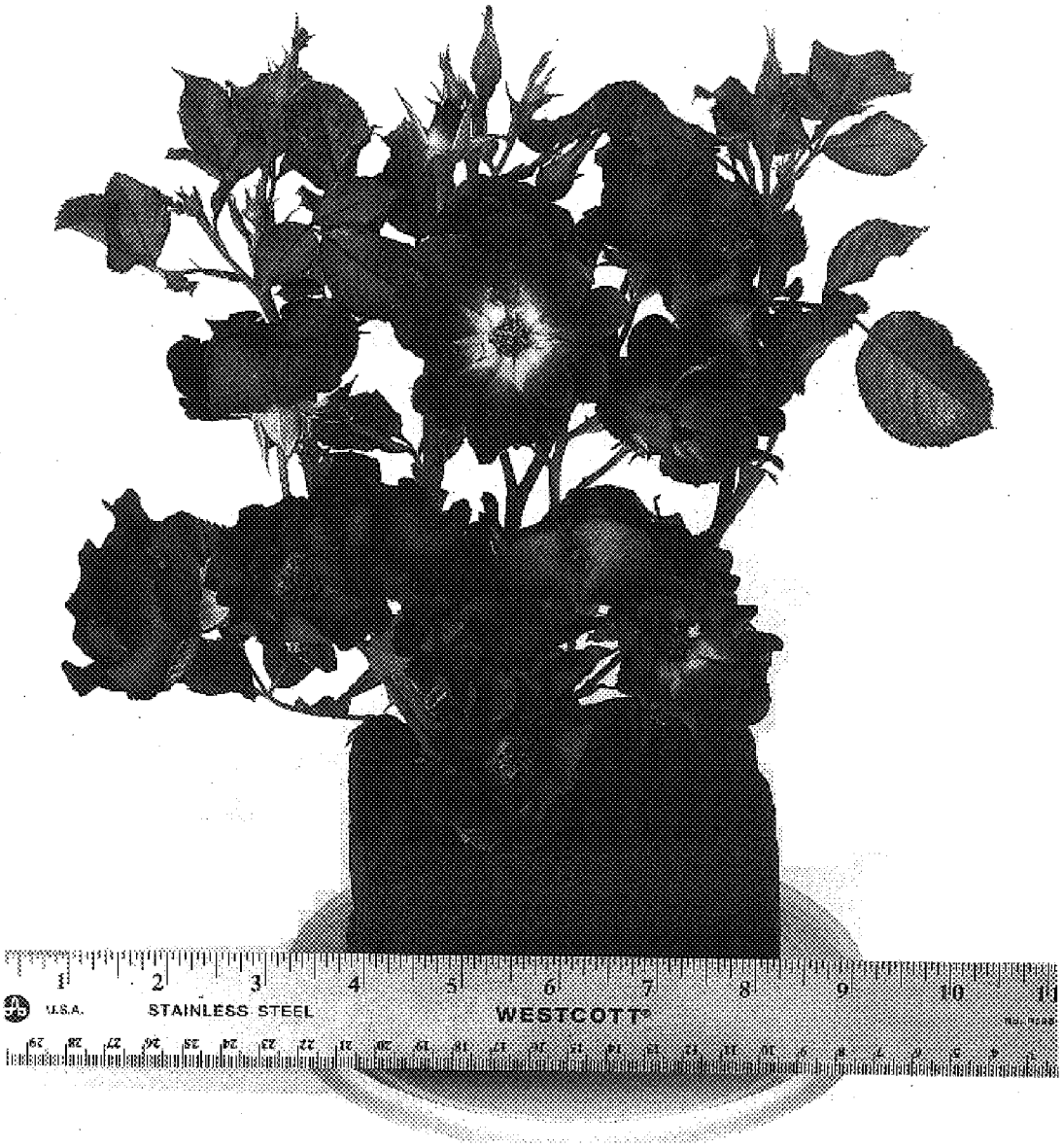
1 2 3 4 5 6 7 8 9 10 11
U.S.A.
STAINLESS STEEL
WESTCOTT